United States Patent
Seals et al.

(10) Patent No.: US 7,762,813 B2
(45) Date of Patent: Jul. 27, 2010

(54) DISPOSABLE PROPHYLAXIS ANGLE

(75) Inventors: Robert G. Seals, St. Charles, MO (US); David M. Hopp, Glen Carbon, IL (US); Steven D. Tripp, High Ridge, MO (US)

(73) Assignee: Young Dental Manufacturing Company 1 LLC, East City, MO (US)

( * ) Notice: Subject to any disclaimer, the term of this patent is extended or adjusted under 35 U.S.C. 154(b) by 0 days.

(21) Appl. No.: 11/890,110

(22) Filed: Aug. 3, 2007

(65) Prior Publication Data
US 2009/0035719 A1  Feb. 5, 2009

(51) Int. Cl.
*A61C 1/07* (2006.01)

(52) U.S. Cl. ...................... 433/124; 433/125

(58) Field of Classification Search .......... 433/114, 433/116, 125, 126, 112, 130, 165, 124; 279/76
See application file for complete search history.

(56) References Cited

U.S. PATENT DOCUMENTS

| | | |
|---|---|---|
| 1,688,410 A | 10/1928 | Chayes et al. |
| 2,226,145 A | 12/1940 | Smith |
| 2,923,060 A | 2/1960 | Staunt |
| 2,983,047 A | 5/1961 | Moulds |
| 3,078,576 A | 2/1963 | Hoffmeister et al. |
| 3,513,550 A | 5/1970 | Ekman |
| 4,643,675 A | 2/1987 | Kuhn |
| 4,963,095 A | 10/1990 | Weissman |
| 4,983,121 A | 1/1991 | Straihammer et al. |
| 5,028,233 A | 7/1991 | Witherby |
| 5,178,538 A | 1/1993 | Eckert |
| 5,531,599 A | 7/1996 | Bailey |
| 5,730,595 A | 3/1998 | Bailey |
| 5,749,728 A | 5/1998 | Bailey |
| 5,902,107 A | 5/1999 | Lowell |
| 5,911,577 A | 6/1999 | Henrikson |

(Continued)

OTHER PUBLICATIONS

International Search Report and Written Opinion for PCT/US08/09219 dated Nov. 5, 2008.

*Primary Examiner*—Cris L Rodriguez
*Assistant Examiner*—Eric Rosen
(74) *Attorney, Agent, or Firm*—McDermott Will & Emery, LLP

(57) ABSTRACT

A dental prophylaxis angle includes a body, a drive gear and a driven gear. The body has a sleeve with an open rear end, a neck, a head, a first axial bore, and a second axial bore. The first axial bore is located in the neck, and the second axial bore is located in the head. The first and second axial bores communicate with each other at an intersection. A channel extends through the body from the base of the neck to the open rear end. The drive gear is adapted to be inserted into said body through said head. The drive gear includes a gear, an intermediate portion and a shaft. The shaft extends rotatably from the open rear end of the sleeve, through the first bore, and into the second bore. The intermediate portion further includes an angled leading edge. The drive gear defines a circumferential groove between said gear and said intermediate portion. The driven gear is rotatably mounted in the head and operatively connected to the drive gear. The body further includes a lip extending into the channel. The lip is adapted to be received by the groove when the drive gear is inserted through said head.

19 Claims, 3 Drawing Sheets

U.S. PATENT DOCUMENTS

| | | |
|---|---|---|
| 6,089,866 A | 7/2000 | Brahler |
| 6,193,514 B1 | 2/2001 | Horan |
| 6,257,886 B1 | 7/2001 | Warner |
| 6,305,935 B1 | 10/2001 | Cardarelli |
| 6,409,507 B1 | 6/2002 | Postal et al. |
| 6,422,867 B2 | 7/2002 | Lang et al. |
| 7,104,794 B2 | 9/2006 | Levy |
| 7,156,659 B2 | 1/2007 | Pernot |
| 2002/0192618 A1* | 12/2002 | Loddeke et al. ............. 433/125 |
| 2006/0154201 A1 | 7/2006 | Braun et al. |

* cited by examiner

DISPOSABLE PROPHYLAXIS ANGLE

TECHNICAL FIELD

The present invention generally relates to dental or prophylaxis angles, and more specifically, to a disposable prophylaxis angle.

BACKGROUND OF THE INVENTION

Dental angles are used by dentists to clean or polish teeth. To accomplish this, dental angles carry dental bits such as prophy cups and brushes and burs. The angle allows dentists to more easily reach various surfaces of a patient's teeth when cleaning or polishing. Angles generally include a body, having a head, which has a major axis angled relative to a major axis of the body. The angle is usually ninety degrees. A drive gear and a driven gear are carried in the body in a meshing relationship. A cap slips over the driven gear and attaches to the body in order to secure the gears within the body. The driven gear generally extends out of an opening in the top of the cap, and carries a desired dental bit, which is used during the cleaning or polishing process. The body is slipped over the nose of a handpiece such as a Doriot type handpiece having a collet which receives the shaft of the drive gear. The collet holds the shaft, and thus the angle, against axial movement. It also connects the drive gear to a motor to rotate the drive gear, which in turn rotates the driven gear and thus the dental bit.

In the past, dentists used nondisposable metal angles. While these were sturdy, they required extensive care to ensure against transferring disease and germs from one patient to another. In use, the head of the angle is inserted into the patient's mouth. This puts the angle into contact with bodily fluid such as saliva and blood. If the metal angle is not properly sealed, the bodily fluids can penetrate the angle. Simply wiping down the metal angle between uses is not adequate sterilization. To properly sterilize the metal angles, the angles must be autoclaved. Additionally, the metal angles must be disassembled periodically and cleaned in order to remove any grit which may have gotten into the angle. If the grit is not removed, it might interfere with the gears, reducing the operating life of the metal angle or making it difficult to operate. Metal angles also require periodic lubrication to ensure their gears run smoothly, quietly, and efficiently to reduce heat build-up. Thus, the care required for metal angles is quite extensive.

Due to the extensive care required by nondisposable angles, disposable ones were desired by dentists. Disposable angles are much more sanitary than nondisposable ones, and therefore more useful in preventing cross-contamination between patients. Their disposable nature eliminates the need to thoroughly sanitize them between each use.

While disposable angles have provided economic and ergonomic benefits in the past, they have not been without problems. The angles often make unwanted noise caused by contact between the drive gear and the shaft of the driven gear. This leads to an unpleasant dental experience for the patient who may already be feeling anxious. Additionally, the unwanted contact causes a rough operation of the gears as opposed to a desired smooth operation. It also causes unnecessary wear and tear on the angle gears, and dentists may need to dispose of the angle sooner than should be necessary. This problem is seen in the angle disclosed in U.S. Pat. No. 5,531,599 ("the '599 Patent"), which is incorporated by reference herein. There is nothing to secure the drive gear within the body. The drive gear is essentially floating within the body. Thus, the angle of the '599 Patent is subject to undesirable noise and vibration caused by unwanted contact between the drive gear and the shaft of the driven gear.

U.S. Pat. No. 5,730,595 ("the '595 Patent") which is incorporated herein by reference, and which is assigned to the same assignee as the present application, discloses a disposable dental prophylaxis angle. The '595 Patent attempts to solve the problems associated with unwanted contact between the drive gear and the shaft of the driven gear by including a finger located on the cap. The finger fits into a groove near the top of the drive gear. The finger extends down from the cap that fits over the head to hold the gears in place. The finger is aimed to prevent axial movement of the drive gear and shaft. However, the finger is located at the top of the angle as opposed to the bottom of the angle. Thus, the finger does not provide axial support for the drive gear. Axial support is desired because the meshing of the gears happens near the top of the angle, creating a downward force on the drive gear. Thus, the finger does not fully accomplish its goal of eliminating unwanted contact between the drive gear and the driven gear shaft. Therefore, an inexpensive disposable angle, which both secures the drive gear within the body and prevents over-flexing of the shaft is needed.

Contra-angles are a specific type of dental angle often used by dentists and hygienists to reach difficult spots on the teeth. Generally, contra-angles include a head angled at an angle greater than ninety degrees. The body is bent at an angle such that the drive gear shaft is bent within the body. The '599 Patent discloses various parts of a disposable dental prophylaxis contra-angle in FIGS. 7-13 thereof. One drawback with contra-angles, such as the one disclosed in the '599 Patent, is that the bending of the shaft makes the shaft susceptible to breakage. During use, the shaft is rotated, and the bending can cause it to over-flex. This over-flexing leads to breakage of the shaft. Additionally, over-flexing of the shaft may cause the shaft to become disengaged from a dental handpiece to which it is attached. Because the inside of the angle body is generally hollow, the shaft has nothing to secure it within the body. If the shaft becomes disengaged, the dental procedure will be disrupted. Therefore, a dental angle which eliminates the problems associated with over-flexing of the drive gear shaft of a contra-angle is needed.

SUMMARY OF THE INVENTION

A dental prophylaxis angle includes a body, a drive gear and a driven gear. The body has a sleeve with an open rear end, a neck, a head, a first axial bore, and a second axial bore. The first axial bore is located in the neck, and the second axial bore is located in the head. The first and second axial bores communicate with each other at an intersection. A channel extends through the body from the base of the neck to the open rear end. The drive gear is adapted to be inserted into said body through said head. The drive gear includes a gear, an intermediate portion and a shaft. The shaft extends rotatably from the open rear end of the sleeve, through the first bore, and into the second bore. The intermediate portion further includes an angled leading edge. The drive gear defines a circumferential groove between said gear and said intermediate portion. The driven gear is rotatably mounted in the head and operatively connected to the drive gear. The body further includes a lip extending into the channel. The lip is adapted to be received by the groove when the drive gear is inserted through said head.

A contra dental prophylaxis angle includes a body, drive gear and a driven gear. The body has a sleeve with an open rear end, a neck, a head, a first axial bore, and a second axial bore. The first axial bore is located in the neck, and the second axial bore is located in the head. The first and second axial bores communicate with each other at an intersection. A channel extends through the body from the base of the neck to the open rear end. The drive gear includes a gear and a shaft. The shaft extends rotatably from the open rear end of the sleeve, through the first bore, and into the second bore. The drive gear further includes an angled leading edge to allow for insertion of the drive gear into the body. The driven gear is rotatably mounted in the head and operatively connected to the drive gear. The body further includes a cradle located within the channel. The cradle extends in the direction of the channel. The cradle engages the shaft of the drive gear to limit the lateral movement of the drive gear within the channel.

In one aspect of the invention an inexpensive disposable angle is provided.

In another aspect, an angle is provided that runs quietly and smoothly.

In an additional aspect, an angle is provided which does not excessively vibrate during operation.

In a further aspect, an angle is provided that will not come apart during operation.

In still another aspect, a contra-angle is provided in which the drive shaft will not be subject to over-flexing during operation.

BRIEF DESCRIPTION OF THE DRAWINGS

A better understanding of the present invention can be obtained by considering the following detailed description and the accompanying drawings in which.

DETAILED DESCRIPTION

Figure 1:
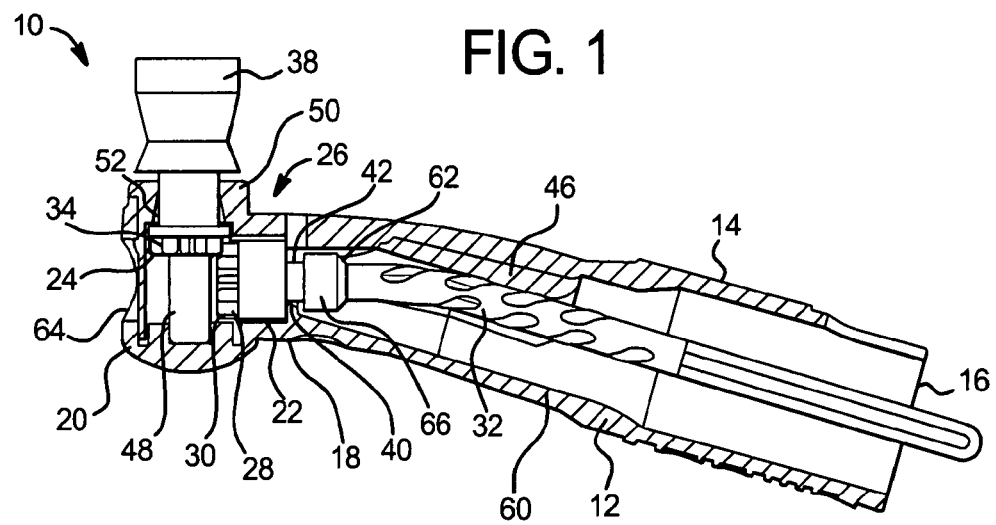
FIG. 1 is a cross-sectional view of an angle of the present invention.

While the present invention is susceptible of many different embodiments, there is shown in the drawings and will herein be described in detail preferred embodiments of the invention with the understanding that the present disclosure is to be considered an exemplification of the principles of the invention and is not intended to limit the broad aspect of the invention to the embodiments illustrated.

Figure 2:
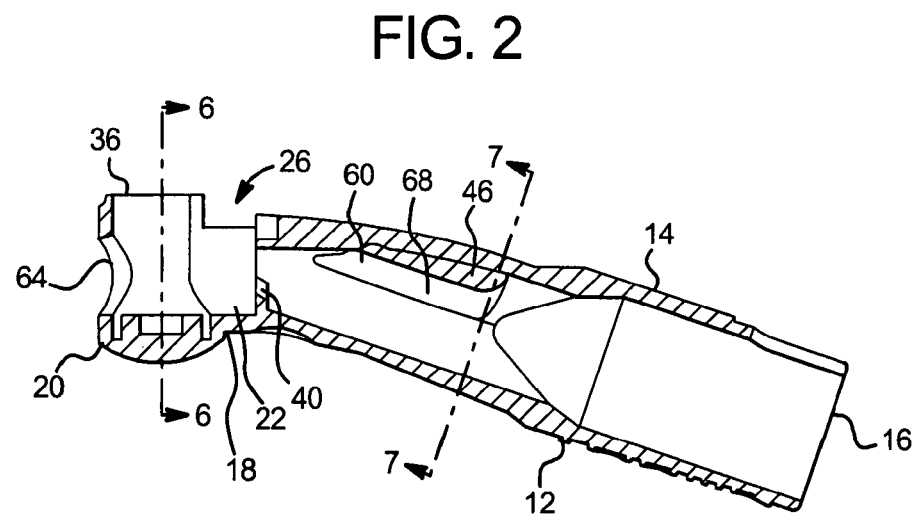
FIG. 2 is a cross-sectional view of the body of the angle of FIG. 1.

One embodiment of angle 10 of the present invention is generally shown in FIGS. 1 and 2. Angle 10 includes a body 12, a drive gear 28, a driven gear 34, and a cap 50. Body 12 includes a sleeve 14, a neck 18, and a head 20. Preferably, the sleeve 14 is formed to have a circular cross-section. The sleeve 14 has an open rear end 16, a neck 18, and a head 20. The head 20 is preferably formed as a cylinder at a right angle to the neck 18. A first axial bore 22 and a second axial bore 24 are located within the body 12. The first axial bore 22 extends through the neck 18, while the second axial bore 24 is located in the head 20. The first and second bores 22, 24 are in communication with each other at an intersection 26 of the head 20 and the neck 18. A channel 60 extends through the body 12 from the base of the neck 18 to the open rear end 16.

Figure 3:
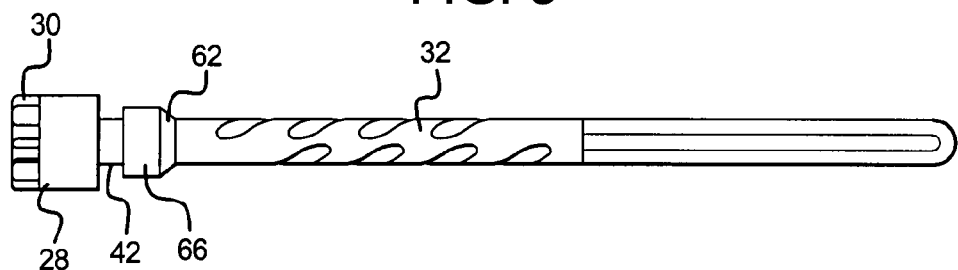
FIG. 3 is a side-view of the drive gear of the angle of FIG. 1.
Figure 4:
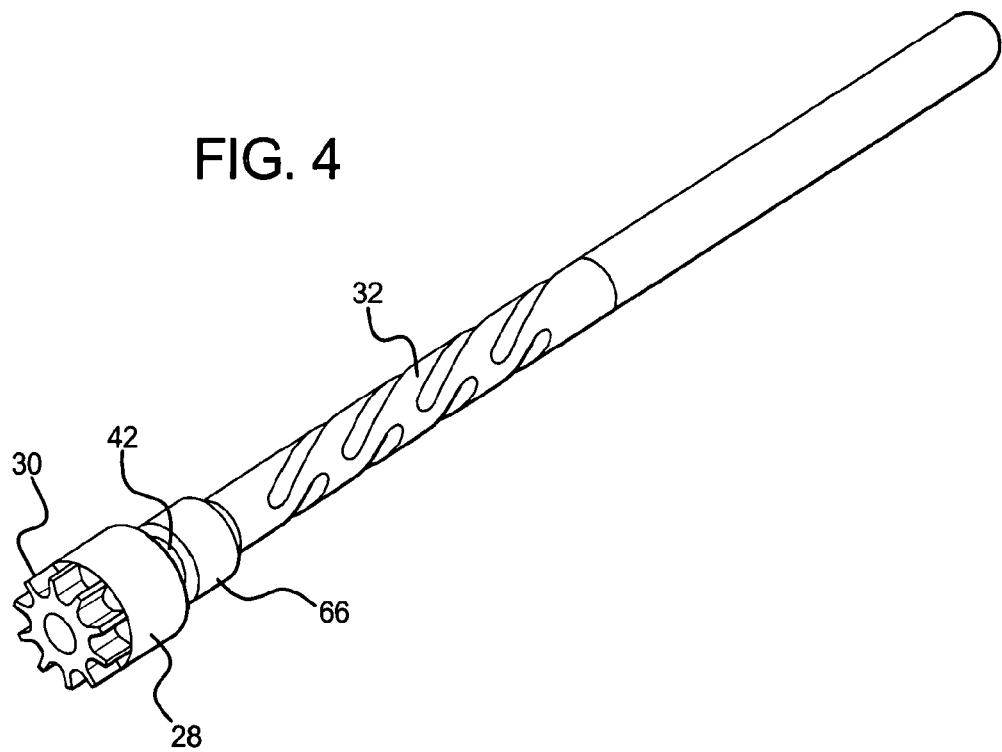
FIG. 4 is a perspective view of the drive gear of FIG. 3.

The drive gear 28, shown in FIGS. 3-4, includes a gear 30, an intermediate portion 66 and a shaft 32. The shaft 32 is preferably flexible for easier assembly of the angle 10, described in more detail below. The shaft 32 may include a plurality of grooves formed at an angle to a longitudinal axis of the shaft 32. The grooves increase the flexibility of the shaft 32. In the assembled position, shown in FIG. 1, the shaft 32 extends rotatably from the open rear end 16 of the sleeve 14, through channel 60, through the first bore 22, and into the second bore 24. For a contra-angle 10, the flexibility of the shaft 32 allows the shaft 32 to bend within the sleeve 14 of the angle 10. Thus, the flexible shaft 32 will accommodate the various angles of the contra-angle 10.

The drive gear 28 further includes a groove 42 located between the gear 30 and the intermediate portion 66. Preferably, the groove 42 is a circumferential recess that surrounds the drive gear 28. When the angle 10 is assembled, as shown in FIG. 1, the groove is located near the head 20. As will be described below, the groove 42 is formed to engage a lip 40 located within the body 12. The intermediate portion 66 is preferably cylindrical, having an angled leading edge 62. The intermediate portion 66 extends from one wall of groove 42 to the end of the angle leading edge 62. The leading edge 62 provides a transition from the larger diameter of the intermediate portion 66 to the diameter of the shaft 32. The leading edge is formed at an angle, preferably 45°, to allow for easier assembly of the angle 10, as described below.

The driven gear 34 is operatively connected to the drive gear 28. The driven gear is rotatably mounted in the head 20. The driven gear 34 is located within the second axial bore 24, and it extends partially out of the head 20 through an aperture 52 of the cap 50. The two gears 28, 34 are positioned substantially perpendicular to one another, such that their teeth are in a meshing relationship. Thus, rotation of one causes rotation of the other.

The cap 50 of the angle 10 is received by head 20. The cap 50 is preferably partially cylindrical in shape. The inside of the cap 50 is hollow such that it can partially surround the driven gear 34 and close aperture 36 of the head 20. The cap 50 may be formed to have a snap-fit connection with the head 20. Preferably, the cap 50 should fit inside the head 20 to form the snap-fit connection. Alternatively, the cap 50 may be formed such that it can be attached to the head 20 in other ways, such as a threaded screw connection, where the cap 50 may attach to the outside of the head 20.

Figure 5:
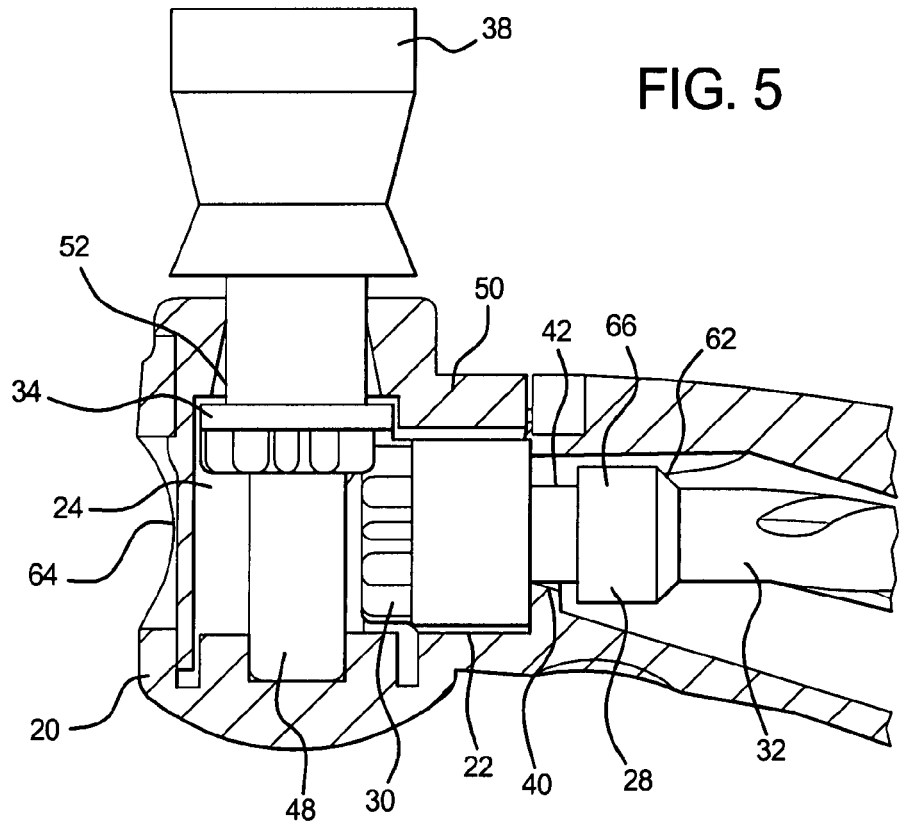
FIG. 5 is a close-up view of the head and neck of the angle of FIG. 1.
Figure 6:
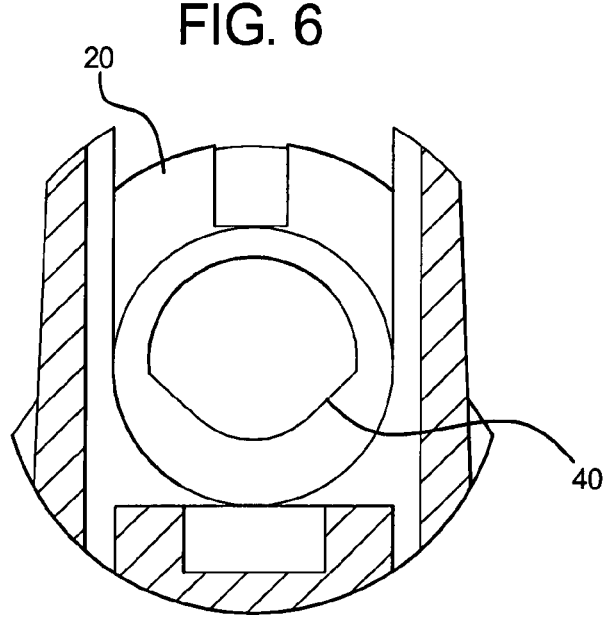
FIG. 6 is a cross-sectional view of the head of the angle of FIG. 2 taken along line 6-6 of FIG. 2.

The angle 10 further includes a lip 40. As shown in FIG. 1, the lip 40 extends from the inner surface of the body 12 and is engaged by the circumferential groove 42 of the drive gear 28. The lip 40, shown in FIG. 5, is preferably formed integral with the body 12 during injection molding. The lip 40 is preferably located at the intersection 26 of the head 20 and the neck 18 of the body 12. While the lip 40 shown in FIGS. 1 and 5 only engages part of the groove 42, it may be formed to engage the entire circumference of the groove 42. Preferably, the lip engages between 90° and 180° of the circumference of the groove 42, but it may engage more or less than this. The groove 42 may be circumferential such that it encircles the drive gear 28. The circumferential shape of the groove allows the lip 40 to continuously engage the groove 42 as the shaft 32 rotates during operation. As shown in FIG. 6, lip 40 is crescent-shaped, such that the center portion of the lip 40 has a smaller radius than the two outer portions. This allows the lip 40 to engage the circumferential shape of the groove 42 during operation. Preferably, the lip 40 is formed such that it extends 180° within the inner surface of the body 12, as shown in FIG. 5. However, the lip 40 may extend more or less than this.

Preferably the width of the lip 40 and the groove 42 are substantially the same so that there will be no excessive movement by the lip 40 within the groove 42 during operation of the angle 10. The width of the groove 42 should however be at least as wide if not slightly wider than the width of the lip 40. This ensures that the groove 42 will be able to receive the lip 40. If the width of the lip 40 is larger than the width of the groove 42, the groove 42 will not be able to engage the lip 40. In determining the width of the lip 40, consideration should be given to the fact that too narrow of a lip 40 creates a risk of breaking the lip 40 during insertion of the drive gear 28 or during operation, due to forces on the lip 40. In one embodiment, the width of the lip 40 is 0.028 in, the width of the groove 42 is 0.049 in., and the groove has a depth of 0.021 in.

The cross-section of the lip 40, seen in FIG. 5 is at an angle, with the angle sloping downward towards the body 12. In one embodiment, the lip 40 is angled at 17°. However, the cross-section of the lip 40 may be at other angles as well.

FIG. 5 also shows the shape of the drive gear 28. As explained above, the intermediate portion 66 has a leading edge 62, which is angled. When the angle 10 is assembled, described in more detail below, the drive gear is front-loaded into the angle 10 through an opening 64 in the head. Thus, the drive gear 28 must pass by the lip 40 until the lip 40 engages the groove 42. The angling of the leading edge 62 allows for easier insertion of the drive gear 28, as the angling helps the leading edge 62 overcome the lip 40. Once the lip 40 engages the groove 42, the gear 30 of the drive gear 28 will not allow for further insertion. The circumference of the gear 30 is too large to slide past the lip 40. Also, once the drive gear 28 has been fully inserted such that the lip 40 engages the groove 42, the circumference of the intermediate portion 66 is such, as shown in FIG. 5, that the drive gear 28 may not be removed from the body 12. Attempts to extract the drive gear 28 would not work because the lip 40 would abut the wall of the intermediate portion 66 opposite the leading edge 62. This wall is not angled, so that removal of the drive gear 28 is prevented.

The engagement between the lip 40 and the groove 42 locks the drive gear 28 into the assembly. The lip 40 maintains the drive gear 28 in a position substantially perpendicular to the driven gear 34. This creates for a proper meshing relationship between the drive gear 28 and the driven gear 34. The lip prevents the drive gear 28 from becoming displaced within the body 12 due to the rotation of the shaft 32. This ensures that the drive gear 28 will not become disengaged from its meshing relationship with the driven gear 34. As mentioned above, creating the lip 40 and the groove 42 so that their widths are substantially close aids in locking them together, thus securing the drive gear 28.

Additionally, the engagement between the lip 40 and the groove 42 prevents unwanted contact between the end of drive gear 28 and shaft 48 of driven gear 34. In prior angles, during operation, the end of the drive gear 28 tends to move toward and contact the shaft 48 of the driven gear 34. This causes unpleasant noise and vibration and creates excessive wear and tear on the angle 10 due to the friction between the shaft 48 of the driven gear 34 and the drive gear 28. To eliminate this, as shown in FIGS. 5 and 6, the lip 40 is preferably located on the lower portion of the first axial bore 22. The lip 40, as reflected in FIG. 5, is located on the opposite the point within the body 12 where the drive gear 28 and driven gear 34 mesh. The engagement between the lip 40 and the groove 42 at this position creates a support for the drive gear 28 and spaces the end of the drive gear 28 from the shaft 48. Thus, the lip 40 and groove 42 together eliminate unwanted noise and vibrations by securing the drive gear 28 within the body 12.

Figure 7:
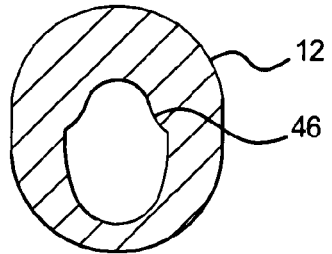
FIG. 7 is a cross-sectional view of the body of the angle of FIG. 2 taken along line 7-7 of FIG. 2.

As shown in FIGS. 1 and 2, a cradle 46 may be located within the channel 60. The cradle 46 is preferably formed integral with the body 12 during injection molding. Shown in FIG. 7, the cradle 46 is circumferential within the body 12 and extends in the direction of the channel 60. When the drive gear 28 is inserted into the body 12, the cradle 46 secures the shaft 32 of the drive gear 28 to prevent lateral movement of the drive gear 28. Specifically, a longitudinal groove 68, shown in FIG. 2, located in the cradle 46 holds the shaft 32 within the cradle 46. The cradle 46 prevents the drive gear 28 from being laterally displaced within the body 12 during operation of the angle 10. Thus, the rotation provided to the shaft 32 will not cause the drive gear 28 to become loose and disengage from the driven gear 34, as the cradle 46 will secure the shaft 32 within the body 12.

In one embodiment, the angle 10 may be a contra-angle 10. The presence of the cradle 46 in a contra-angle 10 is especially beneficial. The added security of the cradle 46 prevents the shaft 32 from over-flexing. Over-flexing is a major problem associated with angles, as it can lead to breakage of the shaft 32. This requires a hygienist or other users to use multiple angles 10 on each patient, which increases costs. Additionally, over-flexing can cause unwanted noise and vibrations, creating an unpleasant dental experience. Thus, by securing the shaft 32 within the body 12, the cradle 46 eliminates over-flexing.

Further, by minimizing the amount of movement of the shaft 32, the cradle 46 ensures that the shaft 32 will stay connected to a dental handpiece (not shown). Dental handpieces are used during operation of the angle. The shaft 32 of the drive gear 28 is connected to the dental handpiece. The dental handpiece provides rotary motion which is transferred to the shaft 32. By reducing the amount of movement of the shaft 32 within the body 12, the shaft 32 of the drive gear 28 will have no room to wiggle out of its connection with the dental handpiece. Thus, the shaft 32 will stay connected to the handpiece and the rotary motion will not be lost. This means the dental procedure will not be interrupted due to loss of rotary motion.

Turning to the assembly of the angle 10, FIGS. 2 and 3 show the unattached body 12 and drive gear 28, respectively, while FIG. 1 shows the angle 10 assembled. To assemble the angle 10, the drive gear 28 is inserted into the body 12 through the opening 64 in the head 20. The shaft 32 is inserted first through the opening 64. The shaft 32 will then be flexed into place within the sleeve 14. The cradle 46 helps to guide the shaft 32 through the sleeve 14 and out the open rear end 16.

As shown in FIG. 1, the shaft 32 has a small enough circumference such that it can slide past the lip 40. As described above, the leading edge 62 of the intermediate portion 66 allows the drive gear 28 to slide past the lip 40 easier. However, once the drive gear 28 is fully inserted, such that the lip 40 engages the groove 42, as shown in FIG. 1, the drive gear 28 cannot be removed. The drive gear 28 cannot be extracted out the same way it was inserted into the body 12 because the lip 40 locks it within the body 12. Also, the gear 30 of the drive gear 28 is too large to be inserted past the lip 40. Thus, once the drive gear 28 is fully inserted into the body 12, such that the lip 40 engages the groove 42, the drive gear 28 is locked within the body 12 and cannot be removed.

Next, the driven gear 34 is inserted into the head 20. The driven gear 34 should be inserted with its gear teeth facing down towards the drive gear 28 until the driven gear 34 and drive gear 28 mesh. The drive gear 28 and driven gear 34 should be substantially perpendicular to each other.

Once the gears are properly positioned, the cap 50 is inserted into the head 20 so that the driven gear 34 cannot be removed. Preferably, the cap 50 is secured to the head 20 with a snap-fit connection; however, the cap 50 may be attached by other means as well. The cap 50 contains an opening 52, receiving part of the driven gear 34.

Next, a dental bit 38 is attached to the driven gear 34 through the opening 52. The dental bit 38 is usually screwed into the driven gear 34; however, other means of attachment may also be utilized. The dental bit 38 is used to clean or polish a patient's teeth. In addition to the dental bit 38, other dental instruments can be attached to the drive gear 34 as is well-known to those skilled in the art.

Once the angle is assembled, it can be used by a hygienist or other dental professional to clean or polish teeth. The shaft 32 of the drive gear 28 extends through the open rear end 16 of the body 12 so that it can be attached to a dental handpiece (not shown). In use, the dental handpiece provides rotary motion to the shaft 32. The rotation of the shaft 32 rotates the drive gear 28. Due to the meshing configuration between the drive gear 28 and the driven gear 34, shown in FIGS. 1 and 5, rotation of the drive gear 28 causes rotation of the driven gear 34. This in turn rotates the dental bit 38, which is used for polishing or cleaning the patient's teeth. When the user is finished, the user may disengage the angle from the dental handpiece and dispose of the angle.

Both the body 12 and the drive gear 28 are manufactured by injection molding using a conventional mold design. This provides for an inexpensive, disposable dental hand tool. As discussed earlier, disposable angles are beneficial because they eliminate the need to sterilize the angle between each patient. Thus, there is no risk of cross-contaminating patients. Further, the use of dissimilar plastics for the body and gears provides for smoother operation of the angle. Preferably the body is made of a hard plastic, such as a polycarbonate resin available from General Electric Co. under the trademark LEXAN, and the gears are made of a more flexible plastic, such as a self-lubricating acetal copolymer available from Celanese Corp. under the trademark CELCON.

While the specific embodiments have been illustrated and described, numerous modifications come to mind without significantly departing from the spirit of the invention, and the scope of protection is only limited by the scope of the accompanying Claims.

What is claimed is:

1. A dental prophylaxis angle comprising:
    a body having a sleeve with an open rear end, a neck, a head, a first axial bore in the neck, and a second axial bore in the head, the first and second bores communicating with each other at an intersection, a channel extends through the body from the base of the neck to the open rear end;
    a drive gear adapted to be inserted into said body through said head, the drive gear including a gear, an intermediate portion and a shaft, the shaft extending rotatably from the open rear end of the sleeve through the first bore into the second bore, the intermediate portion further including an angled leading edge, the drive gear defining a circumferential groove between said gear and said intermediate portion;
    a driven gear rotatably mounted in the head and operatively connected to the drive gear; and
    the body including a lip extending into the channel and adapted to be received by the groove when the drive gear is inserted through said head, the lip restraining the displacement of the drive gear in a first longitudinal direction along the length of the drive gear and a second longitudinal direction along the length of the drive gear, the first longitudinal direction being different from the second longitudinal direction said angled leading edge adapted to engage said lip to allow insertion of said drive gear into said body from said front end of said body until said lip is engaged by said drive gear groove.

2. The angle of claim 1, wherein the engagement between the lip and groove positions the drive gear substantially perpendicular to the driven gear and locks the drive gear within the body.

3. The angle of claim 1, wherein the lip is located at the intersection of the head and the neck of the body.

4. The angle of claim 1, wherein the lip is located opposite the point within the body where the drive gear and driven gear mesh.

5. The angle of claim 1, wherein the lip is crescent-shaped.

6. The angle of claim 1, wherein the engagement between the lip and the groove prevents contact between teeth of the drive gear and a cylindrical portion of the driven gear.

7. The angle of claim 1, wherein the engagement between the lip and the groove creates a load bearing surface.

8. The angle of claim 1, wherein the engagement between the lip and the groove retains the drive gear within the head.

9. A contra dental prophylaxis angle comprising:
    a body having a sleeve with an open rear end, a neck, a head, a first axial bore in the neck, and a second axial bore in the head, the first and second bores communicating with each other at an intersection, a channel extends through the body from the base of the neck to the open rear end;
    a drive gear including a gear and a shaft, the shaft extending rotatably from the open rear end of the sleeve through the first bore into the second bore, wherein the shaft bends along a lengthwise portion thereof within the channel;
    a driven gear rotatably mounted in the head and operatively connected to the drive gear, the driven gear retaining a dental bit; and
    the body including a cradle located within the channel, the cradle having a groove that engages a flexible portion of the shaft of the drive gear, wherein the shaft bends within the cradle to limit the lateral movement of the drive gear within the channel.

10. The angle of claim 9 wherein the cradle prevents the shaft from over-flexing within the sleeve.

11. The angle of claim 9, wherein the cradle secures the connection between the shaft and a dental handpiece, which provides rotary motion.

12. An angle comprising:
    a body having a sleeve with an open rear end, a neck, a head, a first axial bore in the neck, and a second axial bore in the head, the first and second bores communicating with each other at an intersection, and a channel extending through the body from a base of the neck to the open rear end;
    a drive gear adapted to be inserted into said body through said head, the drive gear including a gear, an intermediate portion and a shaft, the shaft extending rotatably from the open rear end of the sleeve through the first bore into the second bore, the intermediate portion further including an angled leading edge, the drive gear defining a circumferential groove between said gear and said intermediate portion, wherein the shaft bends along a lengthwise portion thereof within the channel;
    a driven gear rotatably mounted in the head and operatively connected to the drive gear, the driven gear retaining a dental bit;

the body including a lip extending into the channel and adapted to be received by the groove when the drive gear is inserted through said head; and the body including a cradle located within the channel, the cradle having a groove that engages a flexible portion of the shaft of the drive gear, wherein the shaft bends within the cradle to limit the lateral movement of the drive gear within the channel.

13. The angle of claim 12, wherein the lip is located at the intersection of the head and the neck of the body.

14. The angle of claim 12, wherein the lip is located opposite the point within the body where the drive gear and driven gear mesh.

15. The angle of claim 12, wherein the engagement between the lip and groove positions the drive gear substantially perpendicular to the driven gear and locks the drive gear within the body.

16. The angle of claim 12, wherein the engagement between the lip and the groove prevents contact between teeth of the drive gear from contacting a cylindrical portion of the driven gear.

17. The angle of claim 12, wherein the cradle prevents the shaft from over-flexing.

18. The angle of claim 12, wherein the cradle secures the shaft within the dental handpiece.

19. A dental prophylaxis angle comprising:

a drive gear having drive gear teeth, a circumferential groove and an intermediate portion having an angled leading edge;

a driven gear having a shaft and driven gear teeth for engagement with said drive gear teeth;

a hollow body for receiving said drive gear and said driven gear, said body having a front end and a rear end and including a lip engaged by said drive gear groove for retaining said drive gear within said body such that the lip restrains the displacement of the drive gear in a first longitudinal direction along the length of the drive gear and a second longitudinal direction along the length of the drive gear, the first longitudinal direction being different from the second longitudinal direction, said angled leading edge adapted to engage said lip to allow insertion of said drive gear into said body from said front end of said body until said lip is engaged by said drive gear groove.

* * * * *